United States Patent
Gross et al.

(10) Patent No.: US 10,039,451 B2
(45) Date of Patent: Aug. 7, 2018

(54) SYSTEM AND METHOD FOR OPTIMIZING THE FREQUENCY OF DATA COLLECTION AND THRESHOLDS FOR DETERIORATION DETECTION ALGORITHM

(71) Applicant: KONINKLIJKE PHILIPS N.V., Eindhoven (NL)

(72) Inventors: Brian David Gross, Andover, MA (US); Joseph James Frassica, Andover, MA (US)

(73) Assignee: Koninklijke Philips N.V., Eindhoven (NL)

( * ) Notice: Subject to any disclaimer, the term of this patent is extended or adjusted under 35 U.S.C. 154(b) by 85 days.

(21) Appl. No.: 14/646,030

(22) PCT Filed: Nov. 25, 2013

(86) PCT No.: PCT/IB2013/060376
§ 371 (c)(1),
(2) Date: May 20, 2015

(87) PCT Pub. No.: WO2014/087296
PCT Pub. Date: Jun. 12, 2014

(65) Prior Publication Data
US 2015/0297078 A1    Oct. 22, 2015

Related U.S. Application Data

(60) Provisional application No. 61/732,470, filed on Dec. 3, 2012.

(51) Int. Cl.
*G08C 19/22* (2006.01)
*H04Q 9/00* (2006.01)
(Continued)

(52) U.S. Cl.
CPC .......... *A61B 5/0002* (2013.01); *A61B 5/0022* (2013.01); *A61B 5/7275* (2013.01);
(Continued)

(58) Field of Classification Search
CPC ........................ G06F 19/3418; A61B 5/7264
(Continued)

(56) References Cited

U.S. PATENT DOCUMENTS

2006/0010090 A1*   1/2006   Brockway ............ A61B 5/0002
                                                                706/46
2007/0118054 A1    5/2007   Pinhas et al.
(Continued)

FOREIGN PATENT DOCUMENTS

JP    2008061663 A    3/2008
WO    2004069334 A1   8/2004
(Continued)

OTHER PUBLICATIONS

O'Donoghue, J., et al.; Modified Early Warning Scorecard: The Role of Data/Information Quality within the Decision Making Process; 2011; The Electronic Journal Information Systems Evaluation; 13(3)100-109.

Smith, G.B., et al.; Hospital-wide physiological surveillance—A new approach to the early identification and management of the sick patient; 2006; Resuscitation; 71:19-28.

*Primary Examiner* — Fabricio R Murillo Garcia

(57) ABSTRACT

A method of monitoring a patient includes receiving patient data from one or more sensors a patient monitoring system, comparing the received patient data with preselected thresholds indicative of patient status, determining a patient status from comparing the received patient data with the preselected thresholds, and adjusting a sampling frequency of the one or more sensors based on the determined patient status.

21 Claims, 3 Drawing Sheets

(51) Int. Cl.
*A61B 5/00* (2006.01)
*G06F 19/00* (2018.01)
*A61B 5/01* (2006.01)
*A61B 5/021* (2006.01)
*A61B 5/024* (2006.01)
*A61B 5/0402* (2006.01)
*A61B 5/08* (2006.01)
*A61B 5/11* (2006.01)
*A61B 5/145* (2006.01)
*G16H 50/20* (2018.01)

(52) U.S. Cl.
CPC ............ *G06F 19/3418* (2013.01); *A61B 5/01* (2013.01); *A61B 5/021* (2013.01); *A61B 5/024* (2013.01); *A61B 5/0402* (2013.01); *A61B 5/082* (2013.01); *A61B 5/1118* (2013.01); *A61B 5/14542* (2013.01); *A61B 5/7264* (2013.01); *G06F 19/345* (2013.01); *G16H 50/20* (2018.01)

(58) Field of Classification Search
USPC .................................................... 340/870.07
See application file for complete search history.

(56) References Cited

U.S. PATENT DOCUMENTS

| | | | |
|---|---|---|---|
| 2008/0214904 A1* | 9/2008 | Saeed | A61B 5/0006 600/301 |
| 2009/0312813 A1* | 12/2009 | Cazares | A61B 5/0464 607/14 |
| 2010/0106524 A1* | 4/2010 | Wu | G06Q 40/08 705/3 |
| 2014/0081092 A1* | 3/2014 | McNair | A61B 5/021 600/301 |

FOREIGN PATENT DOCUMENTS

| | | |
|---|---|---|
| WO | 2009/138976 A2 | 11/2009 |
| WO | 2010005779 A1 | 1/2010 |
| WO | 2010/024738 A1 | 3/2010 |
| WO | 2012017354 A2 | 2/2012 |
| WO | 2012085750 A1 | 6/2012 |
| WO | 2012117316 A2 | 9/2012 |

* cited by examiner

SYSTEM AND METHOD FOR OPTIMIZING THE FREQUENCY OF DATA COLLECTION AND THRESHOLDS FOR DETERIORATION DETECTION ALGORITHM

CROSS REFERENCE TO RELATED APPLICATIONS

This application is a national filing of PCT application Serial No. PCT/IB2013/060376, filed Nov. 25, 2013, published as WO 2014/087296 A1 on Jun. 12, 2014, which claims the benefit of U.S. provisional application Ser. No. 61/732,470 flied Dec. 3, 2012, which is incorporated herein by reference.

BACKGROUND

The present application relates generally to patient monitoring. It finds particular application in conjunction with the optimization of the frequency of data collection and thresholds for deterioration detection and will be described with particular reference thereto. However, it is to be understood that it also finds application in other applications, and is not necessarily limited to the aforementioned application.

Undetected patient deterioration in medical institutions has been identified as major safety consideration and cost driver for healthcare worldwide. Many early warning algorithms and deterioration detection systems are available today that are either based on aperiodic data collection (manual spot check vital signs) or via continuous data feed from patient monitoring systems. Studies have shown that typical spot check vital sign workflow is imperfect as the data needed to identify patient deterioration is typically acquired in an uncoordinated fashion which limits the clinical user ability to detect patient deterioration. Further, continuous data feeds increase the burden of the clinical user with workflow impediments such as sensor and leads off conditions, and battery management, requiring the maintenance of continuous physiologic signals to feed the algorithms. Further, existing patient monitoring systems leave the decision of how frequently to collect data and when to calculate a warning score up to the clinical user.

The present application provides a new and improved patient monitoring system which overcomes the above-referenced problems and others.

SUMMARY

In accordance with one aspect, a patient monitoring system is provided. The patient monitoring system includes one or more sensors which sample patient data of a patient at a sampling frequency and a controller configured to receive the patient data from the one or more sensors. The controller programmed to determine a patient status with the patient data and adjust the sampling frequency of the one or more sensors based on the determined patient status.

In accordance with another aspect, a method of displaying medical parameters is provided. The method including receiving patient data from one or more sensors a patient monitoring system, comparing the received patient data with preselected thresholds indicative of patient status, determining a patient status from comparing the received patient data with the preselected thresholds, and adjusting a sampling frequency of the one or more sensors based on the determined patient status.

In accordance with another aspect, a patient monitoring system is provided. The patient monitoring system including one or more sensors which sample patient data of a patient at a sampling frequency and a deterioration detection system which receives the patient data from the one or more sensors, determines a patient status with the patient data, and adjusts the sampling frequency of the one or more sensors based on the determined patient status.

One advantage resides in the optimization of data collection and thresholds for deterioration detection.

Another advantage resides in the reduction of the number of monitoring devices needed to be manually adjusted.

Another advantage resides reducing the number of detected false alarms or event notifications.

Another advantage resides in the reduction of healthcare costs.

Still further advantages of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

The present application is directed to optimizing the frequency of data collection from patient monitoring devices and optimizing threshold for deterioration detection algorithms. With the introduction of wireless smart sensors, data collection can be scheduled, thus removing the clinical user from the schedule decision and optimizing the data acquisition based on patient predisposition for a deterioration event. By optimizing the data sample rate and using the patient predisposition for a deterioration event several advantages can be realized. First, the number of devices needed for monitoring is adjusted based on patient needs. Second, a low risk patient who has a low pre-test likelihood for deterioration may only be monitored every three hours with a pulse and respiration sensor only, thus not requiring electrocardiogram (EKG) arrhythmia and carbon dioxide ($CO_2$) measurements. Not only does this provide a cost effective solution for the hospital as they can make most beneficial deployment of the monitoring assets, but it also minimizes the amount of work needed to maintain the data from the patient. Items like sensors, batteries, and staff time to apply and maintain the system is reduced. Further, the number of false alerts is also reduced if the patient is not measured as frequently.

Figure 1:
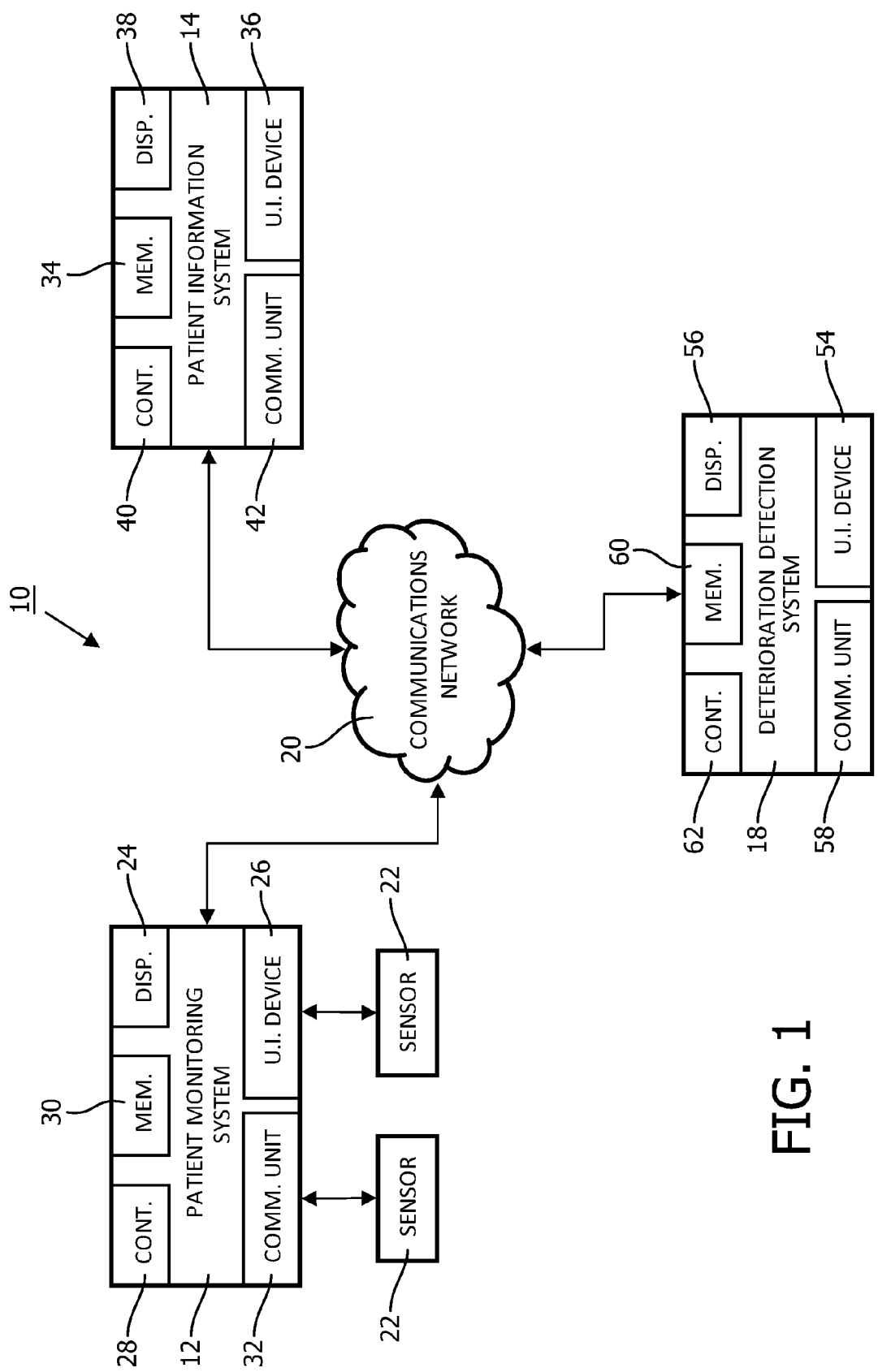
FIG. 1 is a block diagram of an IT infrastructure in accordance with the present application.

With reference to FIG. 1, a block diagram illustrates one embodiment of an information technology (IT) infrastructure 10 of a medical institution, such as a hospital. The IT infrastructure 10 suitably includes one or more patient monitoring systems 12, a patient information system 14, a deterioration detection system 18, and the like, interconnected via a communications network 20. It is contemplated that the communications network 20 includes one or more of the Intranet, a local area network, a wide area network, a wireless 25 network, a wired network, a cellular network, a data bus, and the like.

The patient monitoring systems 12 obtain physiological data for patients (not shown) cared for by the medical institution. The physiological and other data is obtained automatically indicative of measurements of physiological parameters (or vital signs) of the patients, such as heart rate, temperature, blood oxygen saturation, blood metabolite (glucose lactacte etc.), level of activity, and the like. Typically, each of the patient monitoring systems 12 is associated with, and obtains physiological data for, a single patient, but patient monitoring systems associated with multiple patients are contemplated. In some embodiments, it is contemplated that the patient monitoring systems 12 include patient worn monitors and/or beside monitors. The physiological data is typically obtained continuously or intermittently. When the physiological data is obtained continuously or frequently, a trending algorithm (e.g., average, median, peak-finding, etc.) is applied, in one embodiment, to break the stream of physiological data into discrete blocks of physiological data. For example, a continuous stream of physiological data can be separated into blocks of a predetermined duration and a trending algorithm can be applied to each block.

One or more sensors 22 suitably obtain the physiological data. However, it is also contemplated that the physiological data is obtained from other components of the IT infrastructure 10, such as lab equipment, clinical information systems, medication administration record, or electronic medical record, components with user input devices, and so on. The sensors 22 measure physiological parameters of the patients and generate physiological data indicative thereof. In some embodiments, the sensors 22 include one or more electrocardiographic (ECG) electrodes, blood pressure sensors, SpO2 sensors, pulse sensors, thermometers, respiratory sensors, exhaled gas sensors, noninvasive blood pressure (NBP) sensors, metabolite measurements, activity measurements, and the like. Typically, the sensors 22 are disposed on the person of a patient and external to the patient monitoring systems 12. However, sensors local to the patient monitoring systems are contemplated. Where the sensors 22 are external, the physiological data can be obtained via a databus, such as a serial bus, a universal serial bus (USB), or the like; a body coupled network; a Bluetooth, a ZigBee, a wired or a wireless network; a medical body area network (MBAN); or the like. It should be appreciated that the sensors 22 have different sampling frequencies. In one embodiment, the sampling frequencies of the sensors 22 are optimized based on the probability of deterioration and will described with further detail below.

To carry out the above noted functionality, the sensors 22 transmit the measured physiological data via a body coupled network, Bluetooth, wired or wireless network, or the like to a controller 28 of the patient monitoring systems 12. The patient monitoring systems 12 serves as a gathering point for the patient data and/or physiological data measured by sensors 22 and provides temporary storage for the data in a memory 30. The collected physiological data is concurrently transmitted to a controller 28 in the patient monitoring systems 12 which then transmit the physiological data through the communication network 20 to the patient information system 14 where the physiological data is displayed and stored. The controller 28 of the patient monitoring systems 12 also controls a display 24 to display the measured physiological data received from each of the sensors 22 in the corresponding patient monitoring system display 24.

The patient information system 14, such as a central record medical database, receives patient data, treatments, imaging and procedure study results, medication and other interventions, and/or physiological data for the patients and stores the data in one of one or more memories 34 thereof. In one embodiment, the patient data also includes clinical data such as the time of admission, current medications, current clinical problems, current laboratory results, current vitals, past vitals, electronic health records, previous medical history, previous surgical history, and the like. Typically, the data is received from components of the IT infrastructure 10, such as the patient monitoring systems 12 via the communications network 20. However, it is also contemplated that the data is received via one or more user input devices 36 of the patient information system 14. The patient information system 14 also includes a display 38 to display the patient data and physiological data as described above. In some embodiments, the patient information system 14 further displays and/or allows manipulation of the patient data and/or physiological data in the memories 34 using the user input devices 36 and/or the display 38. Additionally or alternatively, in some embodiments, the patient information system 14 further allows components of the IT infrastructure 10 to access the data in the memories 34 via the communications network 20.

The deterioration detection system 18 obtains patient data and physiological data for the patients from components of the IT infrastructure 10, such as the patient information system 14 and/or the patient monitoring systems 12, and/or one or more user input devices 54 of the deterioration detection system 18, and tracks the most recent patient physiological data for each of the patients. As described above, the sampling frequencies of the sensors 22 are optimized based on the probability of deterioration of the patient being monitored. The deterioration detection system 18 calculates a probability of deterioration from the received physiological data and automatically sets the sampling frequency of various sensors 22 of the patient. Further, each time one of the sensors 22 is sampled, the probability of deterioration is recalculated using the most recent physiological data. Based on the recalculated probability of deterioration, the sampling frequency of the sensors 22 can be adjusted. For example, a patient with a low probability of deterioration does not require their sensors be sampled as frequent as a patient with a high probability of deterioration.

Specifically, the deterioration detection system 18 obtains patient and physiological data at the admission of the patient and generates a baseline for the patient. It should also be appreciated that the patient baseline can generated at any time during treatment. After the baseline for the patient has been generated, the deterioration detection system 18 calculates a propensity score for the patient deteriorations and set a probability threshold based on the positive predictive value (PPV) and an alert rate. For example, the PPV is the proportion of positive test results that are true positives (such as correct diagnoses) or the probability that a patient will deteriorate. The PPV is calculated using known methods in the art. An initial probability curve is then calculated by the deterioration detection system 18. It should be appreciated that the propensity score probability function can be based on training data or calculated using the baseline data. In one embodiment, a patient score assesses the current risk band and is obtained through calculation using the physiological data and a scoring table of physiological parameters. The deterioration detection system 18 then determines if the received physiological data crosses into a new risk band. If the physiological data crosses into a new risk band, the deterioration detection system 18 adjusts the corresponding sampling frequency of the sensors 22. In another embodiment, a predicative model determines the potential deterioration of the patient.

In a further embodiment, the probability of deterioration corresponds to a specific deterioration profile. The specific deterioration profiles include physiological parameters of interest and a corresponding preconfigured sampling frequency, a threshold for physiological parameter scoring, risk banding based on the parameters scoring, target probability based on PPV and alert rates, permissive data delay, permissive scoring delay, and the like. After the deterioration detection system 18 calculates a probability of deterioration, the deterioration detection system 18 determines the corresponding deterioration profile and applies the profile to adjust the settings of corresponding sensors 22, patient monitoring system 12, and/or deterioration detection system 18. In some embodiments, the patient deterioration system 18 further includes the user input devices 144 and/or the display 146 allowing a clinician to manually enter patient data and/or other parameters employed by the deterioration detection system 18.

The patient monitoring system 12, patient information system 14, and deterioration detection system 18 include at least one processor, for example a microprocessor or other software controlled device configured to execute patient monitoring software for performing the operations described in further detail below. Typically, the patient monitoring software is carried on tangible memory or a computer readable medium for execution by the processor. Types of non-transitory computer readable media include memory such as a hard disk drive, CD-ROM, DVD-ROM, internet servers, and the like. Other implementations of the processor are also contemplated. Display controllers, Application Specific Integrated Circuits (ASICs), FPGAs, and microcontrollers are illustrative examples of other types of component which may be implemented to provide functions of the processor. Embodiments may be implemented using software for execution by a processor, hardware, or some combination thereof.

Figure 2:
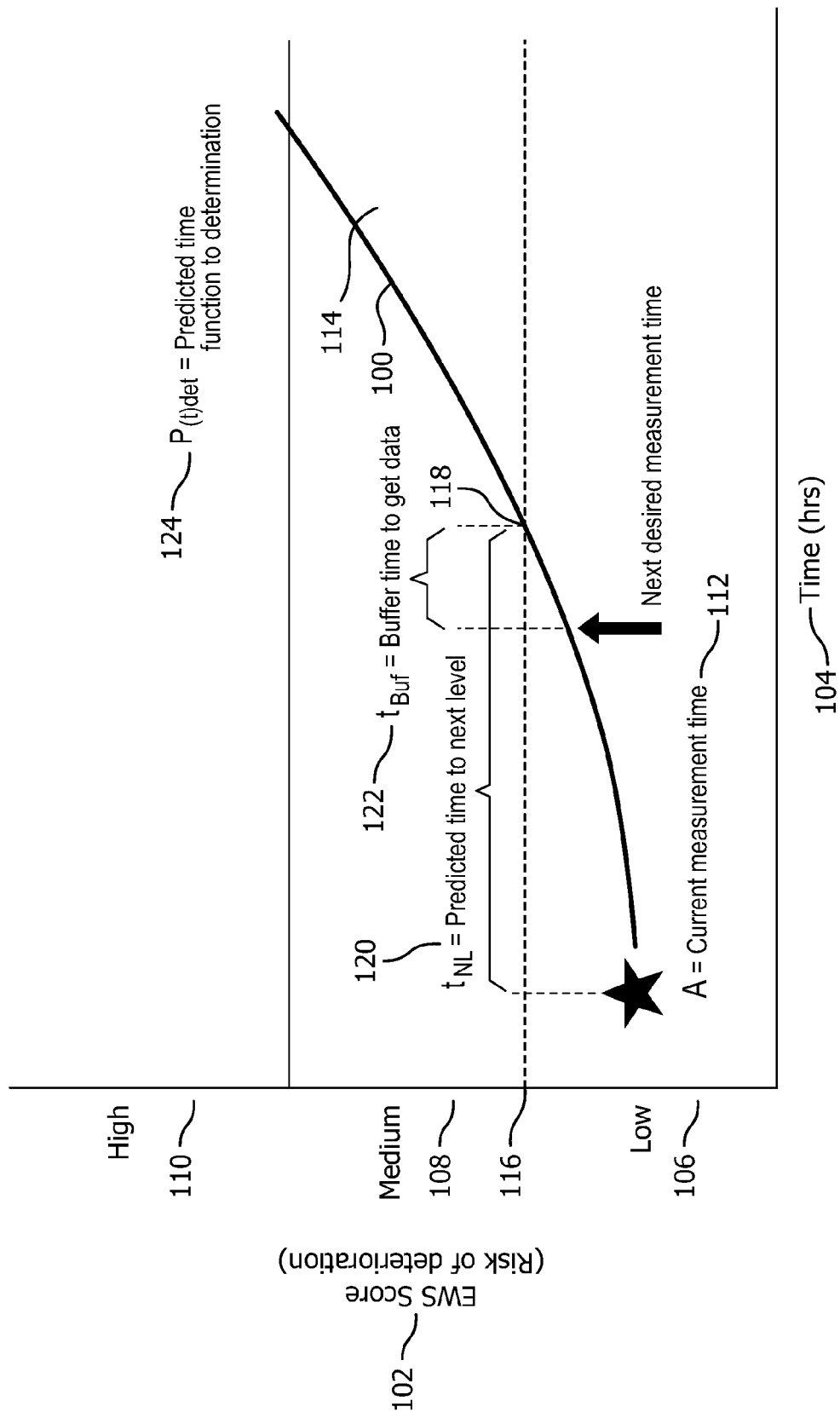
FIG. 2 is a probability of deterioration curve in accordance with the present application.

With reference to FIG. 2, a probability of deterioration curve 100 is illustrated. The probability curve 100 includes an axis 102 indicating the early warning score (EWS) or risk of deterioration and an axis 104 indicating the time in hours. The probability curve includes three different risk bands: low 106, medium 108, and high 110. Once initial patient data and/or physiological data is entered after admission, an initial set of data 112 and risk banding criteria are selected based on optimal positive predictive value (PPV) for detecting deterioration. The initial set of data 112 is also utilized to determine an alarm rate 114 for the patient in the care setting. Once the risk banding criteria and alarm rate are established and based on the propensity scoring, the patient enters a new risk band of the probability curve 100 at threshold 116. The proposed next sampling schedule is based on a predefined probability threshold that the patient will deteriorate before the next schedule measurement at time 118. The probability curve also includes an indicator to the predicted time to the next level $t_{NL}$ 120 and a buffer time to get the next data set $t_{Buf}$ 122. P(t)det is the predicted time function to deterioration.

Figure 3:
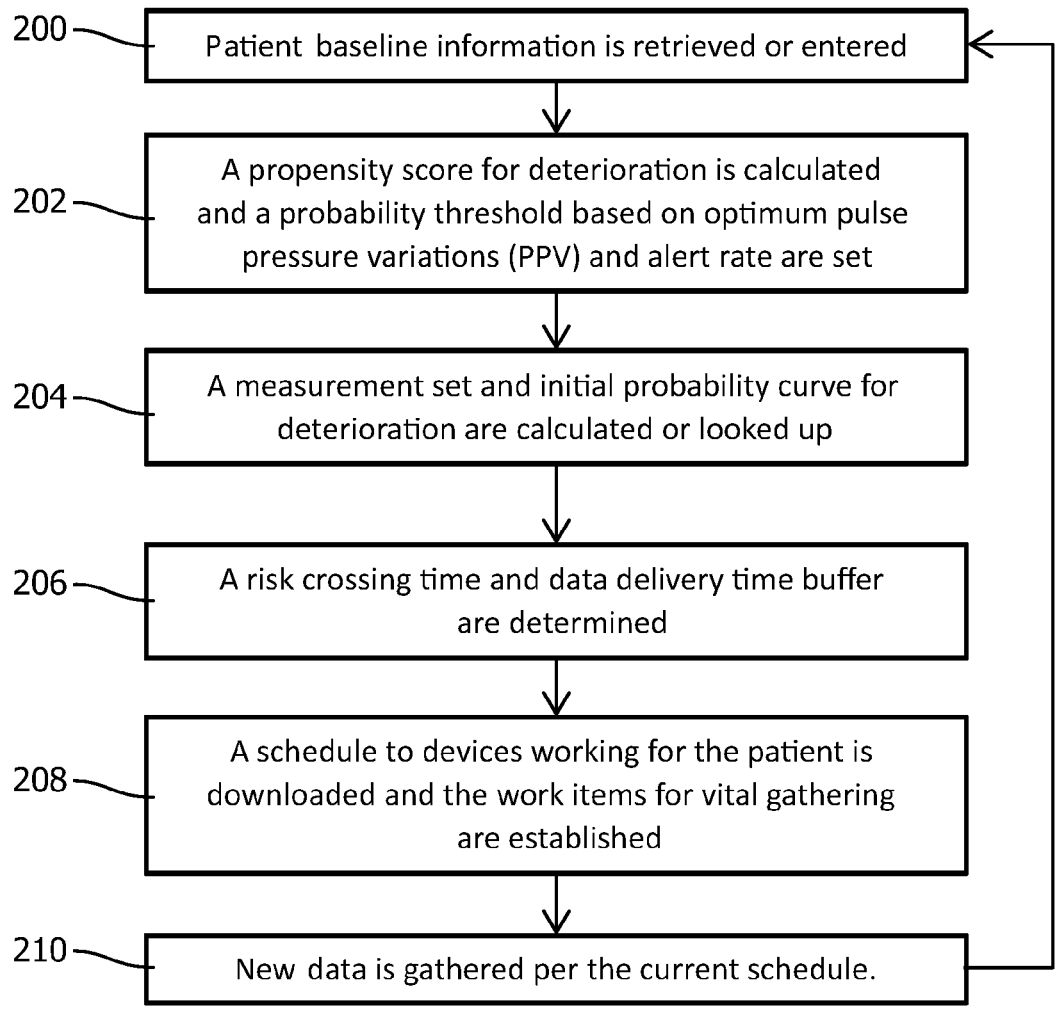
FIG. 3 is a flowchart diagram of the operation of a patient monitoring system in accordance with the present application.

FIG. 3 illustrates one example of steps performed by a processor of the sensor 22. In a step 200, patient baseline information is retrieved or entered. The patent baseline information including age, body surface area, day of hospital admission, sourcing location, history of chronic problems, history of recent surgery, history of recent chemotherapy, current medications, reasons for hospitalization, last set of vitals, and the like. In a step 202, a propensity score for deterioration is calculated and a probability threshold based on optimum positive predictive value (PPV) and alert rate are set. A measurement set and initial probability curve for deterioration are calculated or looked up in a step 204. In a step 206, a risk crossing time and data delivery time buffer are determined. A schedule to devices working for the patient is downloaded and the work items for vital gathering are established in a step 208. In a step 210, new data is gathered per the current schedule. If a new schedule is provided, patient baseline information is retrieved or entered in step 202.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A patient monitoring system comprising:
   one or more sensors configured to sample patient data of a patient;
   a controller configured to receive the sampled patient data from the one or more sensors, the controller programmed to:
   control the one or more sensors to sample the patient data with a sampling frequency;
   determine a patient status with the sampled patient data;
   determine a baseline of the sampled patient data;
   calculate a propensity score for deterioration and probability thresholds based on the baseline of the sampled patient data;
   calculate an initial probability curve from the propensity score and the probability thresholds;
   determine at least one of a predisposition for a deterioration event and a probability of deterioration used to optimize the sampling frequency of the one or more sensors based on the patient status and based on the calculated initial probability curve;
   adjust the sampling frequency based on the determined predisposition for the deterioration event and the probability of deterioration; and
   control the one or more sensors to sample the sampled patient data at the adjusted sampling frequency.

2. The patient monitoring system according to claim 1, wherein the sampled patient data includes at least one of a currently monitored physiological data and an inputted clinical data.

3. The patient monitoring system according to claim 1, wherein the controller is further programmed to determine a patient clinical profile based on the sampled patient data and the at least one of the predisposition for a deterioration event and the probability of deterioration.

4. The patient monitoring system according to claim 3, wherein the controller is further programmed to adjust the sampling frequency of the one or more predetermined sensors which measure parameters of interest according to the patient clinical profile.

5. The patient monitoring system according to claim 1, wherein the patient status is determined by comparing the received patient data against previously received patient data.

6. The patient monitoring system according to claim 1, wherein the controller is further configured to receive clinical data, including electronic medical records, from a patient information system, the controller further programmed to:
   determine the patient status from the clinical data.

7. The patient monitoring system according to claim 6, wherein the clinical data includes electronic medical records.

8. The patient monitoring system according to claim 1, wherein the controller is further configured to display the determined predisposition for deterioration and probability of deterioration and the adjusted sample frequency to a user.

9. A method of monitoring a patient, the method comprising:
   receiving patient data from one or more sensors of a patient monitoring system;
   receiving clinical data from a patient information system;
   comparing the received patient data with preselected patient status thresholds;
   determining a patient status from comparing the received patient data with the preselected patient status thresholds and the received clinical data;
   determining a baseline of the received patient data;
   calculating a propensity score indicative of a probability of deterioration and probability thresholds based on the baseline of the received patient data and the received clinical data;
   calculating an initial probability curve from the propensity score and the calculated probability thresholds;
   determining at least one of a predisposition for a deterioration event and a probability of deterioration based on the calculated initial probability curve; and
   adjusting a sampling frequency of the one or more sensors based on the determined predisposition for the deterioration event and the probability of deterioration.

10. The method according to claim 9, wherein the patient data includes at least one of a currently monitored physiological data and an inputted clinical data.

11. The method according to claim 9, further including:
    determining a patient clinical profile based on the patient and the received clinical data and the at least one of a predisposition for a deterioration event and the probability of deterioration.

12. The method according to claim 11, further including:
    adjusting the sampling frequency of the one or more sensors, the sensors being configured to measure parameters of interest according to the patient clinical profile.

13. The method according to claim 9, wherein the patient data includes at least one of currently monitored physiological data and inputted clinical data and the patient status is determined by comparing the received patient data against previously received patient data.

14. A non-transitory computer readable medium containing software which, when loaded into a processor, programs the processor to
   receive patient data from one or more sensors of a patient monitoring system;
   receive clinical data from a patient information system;
   compare the received patient data with preselected patient status thresholds;
   determine a patient status from comparing the received patient data with the preselected patient status thresholds and the received clinical data;
   determine a baseline of the received patient data;
   calculate a propensity score indicative of a probability of deterioration and probability thresholds based on the baseline of the received patient data and the received clinical data;
   calculate an initial probability curve from the propensity score and the calculated probability thresholds;
   determine at least one of a predisposition for a deterioration event and a probability of deterioration based on the calculated initial probability curve; and
   adjust a sampling frequency of the one or more sensors based on the determined predisposition for the deterioration event and the probability of deterioration.

15. A patient monitoring station comprising:
    one or more sensors via which physiological data is received; and
    one or more processors programmed to
    receive patient data from one or more sensors of a patient monitoring system;
    receive clinical data from a patient information system;
    compare the received patient data with preselected patient status thresholds;
    determine a patient status from comparing the received patient data with the preselected patient status thresholds and the received clinical data;
    determine a baseline of the received patient data;
    calculate a propensity score indicative of a probability of deterioration and probability thresholds based on the baseline of the received patient data and the received clinical data;
    calculate an initial probability curve from the propensity score and the calculated probability thresholds;
    determine at least one of a predisposition for a deterioration event and a probability of deterioration based on the calculated initial probability curve; and
    adjust a sampling frequency of the one or more sensors based on the determined predisposition for the deterioration event and the probability of deterioration.

16. A patient monitoring system comprising:
    one or more sensors which sample patient data of a patient at a sampling frequency;
    a patient information system which receives patient data, treatment, imaging and procedure results, medication, interventions, and physiological data for the patient, the patient information system including a controller, a communication processor, memory for storing the received patient data, at least one or more user input devices, and a display for displaying the patient data;
    a deterioration detection system configured to:
    receive the sampled patient data from the one or more sensors;
    determine a patient status with the sampled patient data;
    determine a baseline of the sampled patient data;
    calculate a propensity score for deterioration and probability thresholds based on the baseline of the sampled patient data;
    calculate an initial probability curve from the propensity score and the probability thresholds;
    determine at least one of a predisposition for a deterioration event and a probability of deterioration to optimize the sampling frequency of the one or more sensors based on the calculated initial probability curve; and
    adjust the sampling frequency of the one or more sensors based on the determined predisposition for deterioration event and the probability of deterioration; and
    a communication network including transmitters and receivers configured to send and receive data.

17. The patient monitoring system according to claim 16, wherein deterioration detection system further determines a clinical profile based on the sampled patient data and at least one of a predisposition for a deterioration event and a probability of deterioration.

18. The patient monitoring system according to claim 17, wherein deterioration detection system further adjusts the sampling frequency of the one or more sensors which measure parameters of interest according to the clinical profile.

19. The patient monitoring system according to claim 16, wherein the sampled patient data includes at least one of currently monitored physiological data and inputted clinical data and the patient status is determined by comparing the received patient data against previously received patient data.

20. The patient monitoring system according to claim 16, further including:
   a controller configured to receive the sampled patient data from the one or more sensors and control the one or more sensors to sample the sampled patient data at the adjusted sampling frequency based on the determined predisposition for deterioration event and the probability of deterioration.

21. The patient monitoring system according to claim 20, wherein the controller is further configured to display the determined predisposition for deterioration and probability of deterioration and the adjusted sample frequency to a user.

\* \* \* \* \*